United States Patent [19]

Chodorow

[11] 4,006,750
[45] Feb. 8, 1977

[54] DISPOSABLE FLOSSER

[75] Inventor: Ingram S. Chodorow, Hartsdale, N.Y.

[73] Assignee: Placontrol Inc., Briarcliff Manor, N.Y.

[22] Filed: Dec. 28, 1973

[21] Appl. No.: 429,654

Related U.S. Application Data

[63] Continuation-in-part of Ser. No. 267,219, June 28, 1972, abandoned.

[52] U.S. Cl. .................................................. 132/91
[51] Int. Cl.² .......................................... A61C 15/00
[58] Field of Search ................... 132/91, 92, 93, 84

[56] References Cited

UNITED STATES PATENTS

| | | | |
|---|---|---|---|
| 2,180,522 | 11/1939 | Henne | 132/91 |
| 2,187,899 | 1/1940 | Henne | 132/91 |
| 2,443,415 | 6/1948 | Buscarino | 132/91 |
| 2,444,697 | 7/1948 | Freyre | 132/92 R |
| 2,517,806 | 8/1950 | Streiler | 132/91 |
| 2,612,177 | 9/1952 | Footer | 132/93 |
| 3,368,553 | 2/1968 | Kirby | 132/92 R |
| 3,860,013 | 1/1975 | Czapor | 132/91 |

Primary Examiner—G.E. McNeill

[57] ABSTRACT

A disposable device for removing plaque and food debris from tooth surfaces, has a handle portion and a bow portion across which a length of dental floss is maintained, the floss, bow, and handle being an integral unit; and the method of manufacturing this complete device in essentially a single operation whereby the handle and bow are molded with the ends of the length of floss disposed and secured in ends of the bow during molding.

6 Claims, 28 Drawing Figures

DISPOSABLE FLOSSER

This is a continuation-in-part application of the now-abandoned patent application having Ser. No. 267,219, and filing date June 28, 1972 now abandoned.

BACKGROUND OF THE INVENTION

This invention is in the field of devices for personal and professional dental care, particularly for removing plaque from the teeth surfaces; the invention is a holder including an integrally attached length of dental floss across a bow, and a method of making this device.

For many years teeth have been cleaned primarily by manual or power-driven brushing; and the spaces between teeth have been cleaned by a variety of methods including brushing, machine-driven jets of water, toothpicks and the like, and by flossing with the commonly available nylon Dental Floss and Dental Tape or similar thread or even rubber bands.

Until recently the most generally accepted objective in cleaning teeth was to remove food particles and chemicals, particularly sweets from tooth surfaces. However, now it has been established and is being taught by a growing number of dentists, orthodontists and periodontists, that the chief cause of caries (dental cavities) and a principal cause of periodontal (gum and root) disease is a bacterial plaque formation that develops on tooth surfaces. When removed, new plaque can reform in less than 24 hours. The causes of plaque development are not fully appreciated; however, a person's normal body chemistry independent of his particular diet, can be a contributing factor.

Plaque is the name given to a bacterial substance that begins as an invisible film of micro-organisms, and with saliva and foods, particularly sugars, forms a soft sticky white film on the surfaces of teeth and between teeth. If plaque is not removed daily it can develop and harden into a firmly attached substance called calculus or tartar, which may cause gums to redden and swell in a condition known as gingivitis. This disease is often characterized by receding gums, which causes the creation of small pockets around the teeth which trap food particles and bacteria. These pockets can enlarge if the gums become further inflamed or infected causing the bone supporting the teeth to become infected and destroyed. The weakened tissue is infection-prone and once so injured the gums cannot protect the underlying bone from the spread of this disease. Additionally, bacterial plaque produces noxious chemicals which cause cavities and irritate the gums. This is the manner in which teeth become loosened and ultimately lost, the latter stages here-described being periodontal disease.

Of the methods mentioned above for cleaning teeth, brushing is not effective to remove plaque on interdental tooth surfaces between the teeth; water jets are not sufficiently abrasive to achieve plaque removal, though they may remove food particles very well; also, toothpicks are too thick and cumbersome to probe and scrape between two closely adjacent surfaces. This leaves only dental floss, a strand of multi-filament nylon that is moved in a sawing action into the crack or space between the sides of two teeth. The unwaxed version of dental floss is less smooth and thus more abrasive and more effective to scrape plaque off the tooth enamel surfaces in question. However, the user of any floss has the problem of maneuvering it — while under certain tension, down between each pair of teeth, including the rear-most teeth. Positioning the floss is inconvenient in most teeth locations, quite difficult in many, and almost impossible in others. The procedure generally includes winding opposite ends of a strand around one finger of each hand respectively, then inserting these two fingers of both hands into the mouth, and attempting to position the span of floss between the fingers in the desired location, and finally reciprocating the floss between teeth while also moving it vertically along the tooth from tip to gum. The floss is maneuvered preferably just under the edge of the gum, held firmly against the proximal surface of the tooth and pulled over its surface toward the chewing edge.

It is known from surveys that most people, even including those who take seriously the matter of dental care and brushing regularly, do not use floss daily, because the technique for use, as described above is so tedious. For a number of years there have been attempts to render flossing less tedious and also to render it more effective, by the development of holders onto which floss is attached. Most holders have two arms across which the floss is strung; however, secondary complications with the holders themselves have resulted in general no-use, and thus there has been no remedy to the original problem of non-use regularly of floss held by hand.

One basic problem with the holders is that floss eventually frays, becomes thin, and breaks after being used. Whether the floss holds up for five, 20, or more teeth depends upon the tightness of the interdental spaces and the abrasion the floss suffers. By the original, manual operation, the floss user merely pulled the exposed end of floss from a spool, cut off a segment, then wound the cut segment on his fingers. With certain floss holder devices, the user must, for each flossing operation, obtain a length of floss, thread or carefully position it about a floss holder, pull on some part of the floss until it is in tension, and finally secure it under tension to the holder. Whether a floss supply is provided on a spool in the holder handle according to one device, or provided from a separate spool from which segments of floss are cut as needed, the remaining threading and tensioning procedure is still an inconvenient burden.

An additional, unsuccessful approach to the flossing problem has been to manufacture flossers, each with its own pre-cut length of floss attached or attachable under tension to the holder. In one device an elastic band was stretched and secured in tension to a frame. In another device the arms of a pre-made holder are flexed toward each other; then while the tip of each arm is temporarily plasticized, a length of floss is secured to these tips, and later the arms are released whereby they spring outward away from each other to establish tension in the floss.

Even this pre-strung type of flosser has inherent features that contribute to the general non-use of flossers by the public. The holders of these flossers are made independently of the floss, and in a separate operation the floss is positioned and secured in tension on the holder. The manufacturing steps of separate attachment and tensioning of the floss to the holders increases the retail price such as to add to the already existing consumer resistance to using these devices. As already discussed the holders that must be threaded, tensioned and secured by the user, require interest, patience and skill which combination of traits is rarely found.

SUMMARY OF THE INVENTION

According to the present invention it was discovered that tension of the floss in the holder at the time of manufacture, or even just before use, is not required, because tension is established automatically after the floss is inserted into the space between two teeth. During insertion of the floss and later during sawing action, any slack in the floss is taken up as soon as the holder is positioned such that the point of teeth-floss contact is outside the line extending between the two tips of the holder arms, with the floss thus formed into a wide angle ∨. Clearly the floss can be maintained in tension during use, as it becomes stretched between three points, namely the two tips of the holder and the point of contact where the floss engages two teeth. For some users this slack that allow three-point tension, is even advantageous as it provides greater latitude in positioning the holder; the floss can then be partially wrapped around and conformed to curved surfaces of a tooth to scrape a greater amount of surface, in contrast to a strand of floss in tension that tends to retain its straight-line-configuration, minimizing its degree of contact with curved tooth surfaces.

Where two teeth have their adjacent surfaces very close together forming a tight interdental space, it may be difficult to maneuver and force a strand of floss down between these teeth to the gum. For this type of situation it can be helpful to use a different embodiment of the new invention, wherein the floss is placed in tension during manufacture, such that the floss "in a straight-line configuration" is tensioned between the holder arms, as contrasted with floss in tension only after being formed into a V-shaped configuration while engaging the teeth. With this alternate embodiment the floss is taut in all positions and orientations of the holder, which is helpful to some users, especially where tight spaces are prevelant. In the embodiment where tension of the floss is established during manufacture, this added tension helps compensate for any tendency for slack to develop where shrinkage of the plastic occurs during solidification. In fact the arms can be designed so that if shrinkage is unavoidable, it will occur more severely in selected areas to cause the arms to shrink or warp away from each other and thus stretch the capture floss between said arms.

The new invention is a floss holder device designed to be disposable, i.e., to be thrown away after a user "flosses" some or all of his teeth; the new invention further provides a method of making these yoke-like holders with the floss attached in a single manufacturing step which greatly reduces cost. According to this method, floss is positioned in a multi-cavity mold, prior to injection molding of a suitable plastic into the cavities. The resulting product is complete and ready for use with no requirement of an additional step of threading, tensioning, or securing floss; also it can be considerably less expensive than all other known holders which are designed to have the floss attaches separately and furthermore tensioned.

Another feature of this invention is an intentional creation of flashing in the arms of the holder where the floss exits the arms. Ordinarily in any injection mold the adjoining parts which define the boundaries of a mold cavity, are designed to close together tightly, and thereby to effectively seal the cavity space. By the present invention an imcomplete seal is specifically created at said exit points of the floss from the holder arms; consequently a small quantity of plastic flows out of the cavity at each exit point and flows for a short distance along and around the floss. When the holder solidifies and is ejected from the mold, a sheath of plastic partially or completely surrounds the floss at its two ends where they exit the holder's arms. The sheath serves primarily to eliminate any sharp edge that would otherwise exist at this juncture; it is here that high stress concentrations develop on the surface of the floss when a strong force is applied to the floss normal to its axis, as occurs in normal use. This sheath provides support in the form of reactive forces opposing the applied normal force, on all surfaces 360° around the floss; furthermore this support force remains effective even when the floss is displaced by the stress generated during usage because of the flexibility or pliability of the flashing.

Another function of the sheath is to increase the surface area of the floss contacted by the solidified plastic of the holder. Thus considerable friction is established between the floss and the arms and sheaths in which it is embedded; such friction restrains the floss from being pulled out of the arms during use when high tension forces develop axially in the floss, tending to separate it from the holder arms. The flashing thus helps to stabilize the floss at its junctures with the arms by reducing certain deflection, eliminating sharp edges at the areas of deflection, and preventing an abrupt change of direction of the floss at this juncture which helps maintain the floss in tension loading as opposed to shear loading where it is not as strong.

In partial summary, it has been discussed that plaque removal is a physical problem, but like seat belts in automobiles, the persons whose bodies are in jeopardy have a manual difficulty and a resulting psychological resistance to utilizing floss which can greatly or totally overcome the problem. Thus, the present invention of a floss holder that is ready for use and the new and inexpensive method of manufacturing this holder, constitute an advance in dental care.

As will be shown in the drawings and descriptions to follow, there are numerous embodiments of flossers and methods for making these flossers within the scope of this invention.

DESCRIPTION OF THE PREFERRED EMBODIMENT

Figure 1:
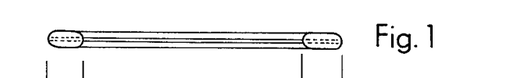
FIG. 1 is a top plan view of the new flosser.
Figure 2:
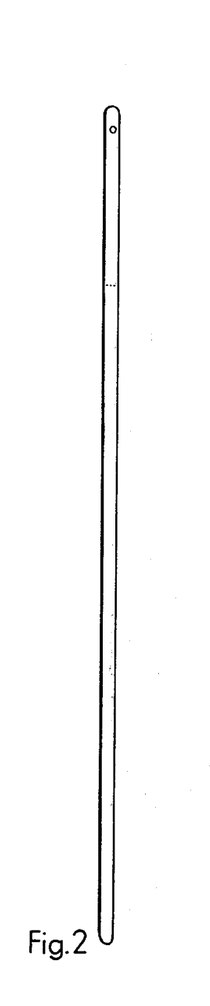
FIG. 2 is a side elevation view thereof.
Figure 3:
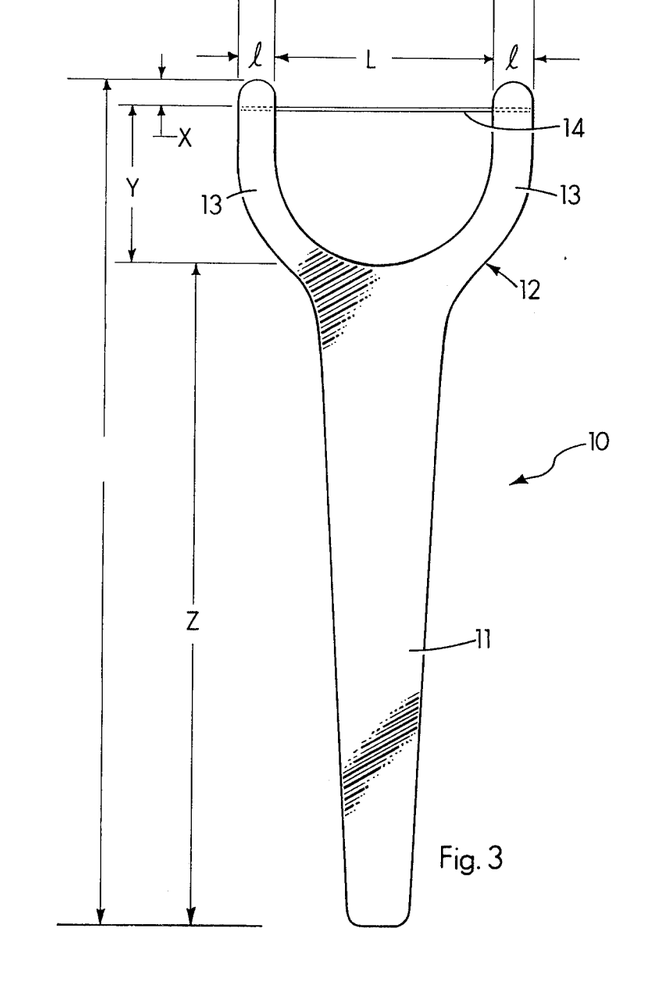
FIG. 3 is a front elevation view thereof.
Figure 4:
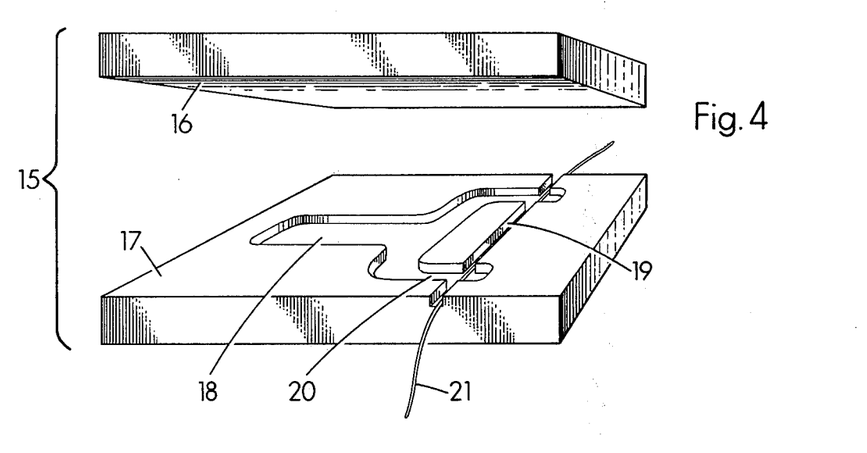
FIG. 4 is a front perspective view of a single cavity injection mold for making the new flosser.
Figure 5:
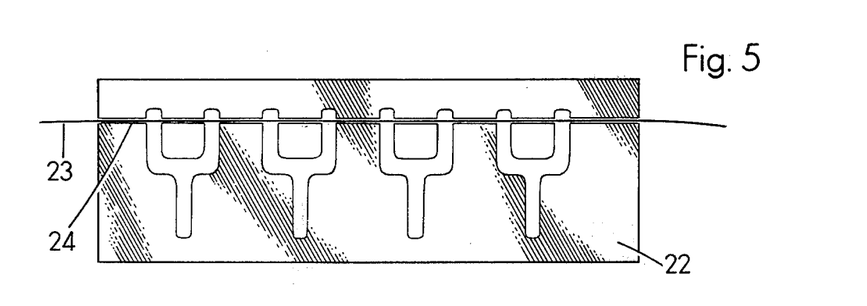
FIG. 5 is a top plan view of a multiple-cavity mold similar to FIG. 4.
Figure 6:
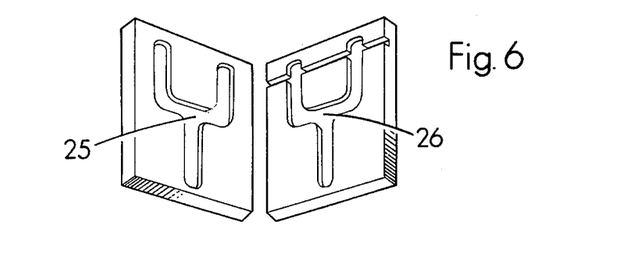
FIG. 6 is a top plan view of another embodiment of a single-cavity mold.
Figure 19:
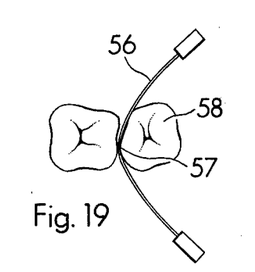
FIG. 19 is a top plan view in section of a flosser with slack in the floss.
Figure 20:
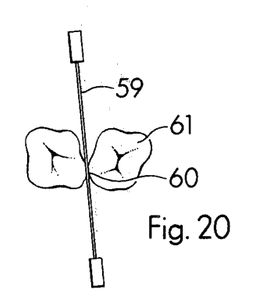
FIG. 20 is a top plan view in section of a flosser with the floss in tension.

A first of various preferred embodiments of the device of this invention is shown in FIGS. 1–3, and a first preferred method of manufacturing various embodiments of the device is shown in FIGS. 4–6. The device in FIGS. 1–3 is a frame 10 having a handle part 11 and a generally U-shaped bow part 12 with arms 13 spaced apart and extending from one end of the handle part. Spanning the arms 13 and permanently secured to their tips 14 is a strand of floss having length L between the arms and length $l$ within each arm. The handle and arms constitute a one-piece injection-molded plastic frame or holder, with the ends of the floss $l$ embedded within the arm tip 14 as shown in the Figures. This strand of floss has a generally longitudinal configuration, but it is not in tension, and therefore the arms 13 to which the floss is secured are neither flexed nor under any external bending stress from the floss. Thus the strand has length essentially the same as the length L of the space between the arms 13, this length being chosen to be a size convenient for inserting into the mouth; alternatively the strand has length greater than L, thus providing a degree of slack to the floss. In use the strand can be maneuvered into the space between the adjacent side surfaces of two teeth, and moved downward to the gum below. As shown in FIG. 19, where the central part 56 of the floss has slack and thus is non-linear, the floss in use can conform to and scrape much more curved surfaces 57 of a tooth 58 than is possible with a floss 59 in tension in FIG. 20 which contacts the small area 60 of tooth 61. The distance X in FIG. 1, from the strand to the tip of the arm is very small, and the distance Y is at least as great as the average height of teeth measuring from the gum to the tip. The handle length Z can vary for convenience, its function being to permit a user to hold and manipulate the device with only one hand, and thus avoid the necessity of inserting fingers of both hands into his mouth to hold the floss.

According to the preferred method of manufacturing shown in FIGS. 4–6, a typical mold 15 shown schematically, having top and bottom parts 16 and 17 with one or more yoke-shaped cavities 18, is used in an injection-molding process. In FIG. 4 the cavity 18 is formed in only the bottom half of the mold, with a trough 19 situated transverse of the limbs 20 of the cavity, the location of the trough corresponding to the desired location of the floss span of the holder. Immediately prior to injection of fluid plastic into the cavity 18, a length of floss 21 is positioned in the trough, so that it extends across the width of each limb of the holder, with sections $l$ (see FIG. 1) of the floss within each limb, and section L of the floss extending between the two limbs. During injection section $l$ of floss will become embedded and secured in the molded plastic; during this molding fluid plastic necessarily flows into a cavity, and flows about and around the floss therein, coating the outer peripheral surfaces of the floss which become embedded therein. Upon hardening of the plastic a solid holder is formed with the floss secured therein. In this manner the holder is formed and the floss attached in a single step, as opposed to a two-step operation of (a) making the holder, and (b) attaching floss to an existing holder. Here, initially the holder does not exist; then in a single step the holder is formed about the floss, as opposed to attaching floss to a holder. For reasonable economy a multi-cavity mold 22 of FIG. 5 would be used with a longer length of floss 23 positioned in trough 24 prior to injection. The placement of the floss in the trough can be done by any convenient method, with no tension of the floss required. FIG. 6 shows a variation of the mold with cavities 25 and 26 formed in both halves of the mold.

Figure 7:
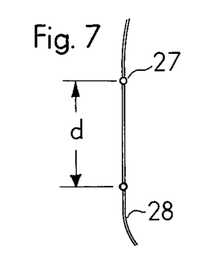
FIG. 7 is a top plan view of a length of floss with beads attached.
Figure 8:
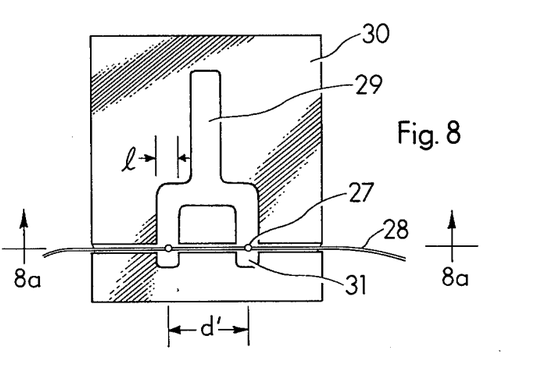
FIG. 8 is a top plan view of a mold including the floss of FIG. 7 for a second embodiment of a flosser.
Figure 8A:
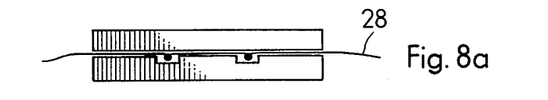
FIG. 8a is a front elevation view of FIG. 8.
Figure 9:
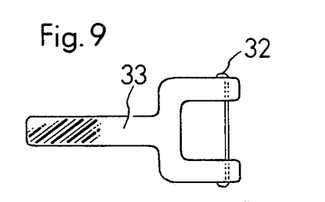
FIG. 9 is a top plan view of a third embodiment of a flosser.

A number of different techniques are available to restrain the floss more securely within the two limbs of the holder, where such may be desired. FIG. 7 shows beads 27 fastened on floss 28 or formed as knots, loops, or other enlargements of the floss itself. The beads are spaced apart a distance $d$ in FIG. 8 corresponding to the center-to-center distance $d'$ between the two limbs of cavity 29 in mold 30. After the beaded or knotted floss is positioned to traverse the mold, and injection is complete, section $l$ of the floss and the beads 27 are permanently embedded in the limbs 31. Beads may be fastened onto the floss by mechanical crimping, or cementing, or any other feasible method. A simpler technique would be to merely place a drop of cement or appropriate solvent at 32 where the floss extends out of the limb 33 in FIG. 9, or a bead or knot at 32.

Figure 10:
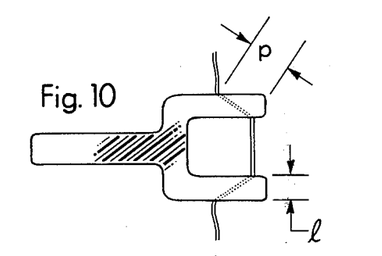
FIG. 10 is a top plan view of a fourth embodiment of a flosser.
Figure 11:
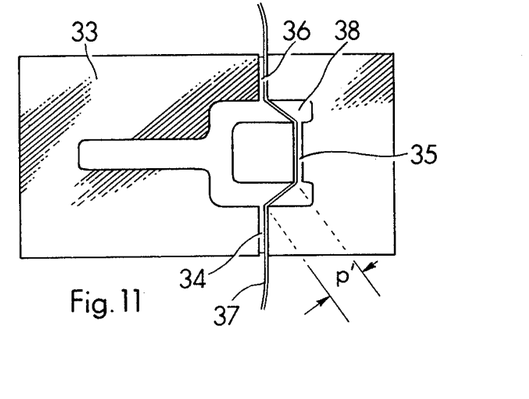
FIG. 11 is a top plan view of a mold for making the flosser of FIG. 10.

Instead of auxilliary elements such as beads or cement, two representative arrangements are shown in FIGS. 10 through 13 for extending the floss for a greater length within each limb of the holder to achieve a greater frictional restraint on the sections of floss embedded in these limbs. In FIG. 10 the floss lies diagonally for length $p$ which is far greater than width $l$ through a limb as exists in FIGS. 1 and 10. A mold 33, to position the floss in this diagonal orientation, is shown in FIG. 11 where the trough has three parts 34, 35 and 36; when the floss 37 is aligned in this trough, section $p'$ of the floss will necessarily take the diagonal position shown within limb 38 of the cavity and produce the flosser of FIG. 10.

Figure 12:
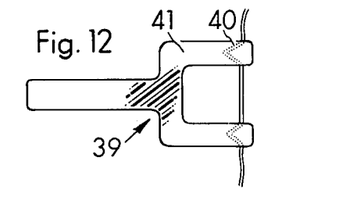
FIG. 12 is a top plan view of a fifth embodiment of a flosser.
Figure 13A:
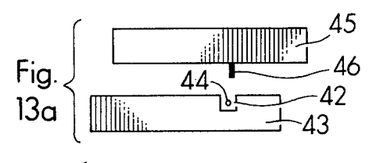
FIG. 13a, 13b, 13c, are side elevation views of a mold for making the flosser of FIG. 12.
Figures 13B, 13C:
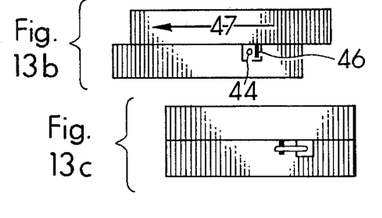

FIG. 12 shows still another embodiment 39 of the flosser with the floss formed into a V-shaped 40 within limb 41, thus providing greater length of embedded floss and resulting greater frictional restraint thereon. Referring now to FIGS. 13a, 13b, and 13c, the trough 42 in bottom mold 43 with floss 44 therein, is essentially the same as in FIG. 4, but the upper part of the mold 45 has two pins 46. In use the top 45 is laterally displaced relative to the bottom as shown in FIG. 13a and floss 44 is positioned normally and top 44 is closed as in FIG. 13b with pin 46 on the right side of floss 44; finally top 45 is moved rearward in the direction of arrow 46 to the position shown in FIG. 13c, dragging the floss 44 into the U-shaped 40 shown in FIG. 12.

Figure 14:
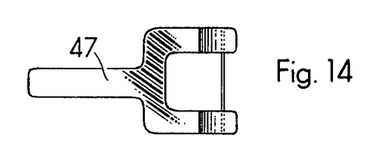
FIG. 14 is a top plan view of a sixth embodiment of a flosser.
Figure 14A:
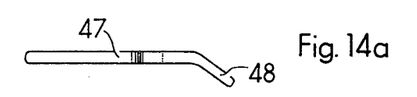
FIG. 14a is a side elevation view of FIG. 14.
Figure 15:
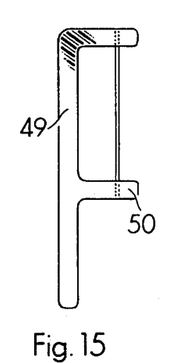
FIG. 15 is a top plan view of a seventh embodiment.
Figure 15A:
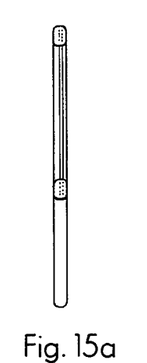
FIG. 15a is a side elevation view of FIG. 15.
Figure 16:
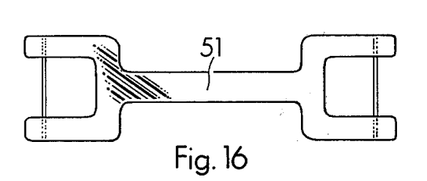
FIGS. 16, 17 and 18, are top plan views of three other embodiments of flossers.
Figure 17:
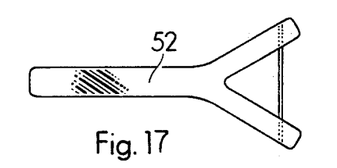
Figure 18:
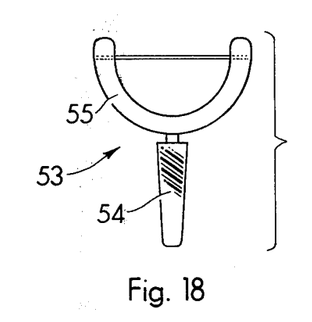

Regardless of the molding arrangements selected, the overall shape of the holder may be varied as shown in FIGS. 14–18: holder 47 in FIG. 14a has downward angled limbs 48; holder 49 in FIG. 15 has short lateral limbs 50; holder 51 in FIG. 16 has limbs and floss on both ends; holder 52 in FIG. 17 has V-shaped limbs; and holder 53 in FIG. 18 has separable handle 54 and bow 55. A further embodiment of this invention utilizes any of the above holders manufactured generally as described, but with the floss placed in tension during manufacture and maintained in tension thereafter. Tension is easily established, as indicated schematically in FIG. 21, by applying opposing axial forces $F_1$ and $F_2$ to the end portions 61, 62 of the floss extending out of the mold 63. An alternative way to create the desired tension is to design each arm of a holder to be thinner on the outer edge than the inner edge; the thinner edge will cool and solidify more quickly, and the shrinkage of this edge before the inner edge will cause the arm to tend to warp outward. If both arms warp outward and away from each other, the floss between them will be placed in tension. The amount of tension will depend of course on the amount of shrinkage and warpage and the strength of the material. In the earlier-described embodiments having taut floss, the amount of tension depends partially upon the amount of tension applied during manufacture, and partially upon the strength of the arms due to material selection and structural design to refrain from bending inward. Also attachment may be done by fusing the floss to the holder, or attachment may be totally eliminated by forming the strand of the same material that is injection molded to form the holder. Also abrasive or talc, asbestos, or glass can be added to the injected plastic to improve its capacity for gripping the strand. All of the above described molds and their gates, runners, etc., should be designed accordingly to standards of the industry. Thus the molds and cavities shown in all of the Figures are schematic or representative, but in actual practice would include gates, runners, flues, etc., and tight seals to all boundaries of the cavities to prevent fluid plastic from flowing out of the cavity.

It is an objective in good injection mold design to produce parts with a minimum of flashing, which is of course, bits of plastic that leaked out of the mold cavity and remain on the solidified piece as tiny projections or tits. Such flashing is unattractive, can interfere with function, and can even be dangerous on pieces which are handled; and in all these cases it must be removed at considerable expense and inconvenience.

Figures 21, 22:
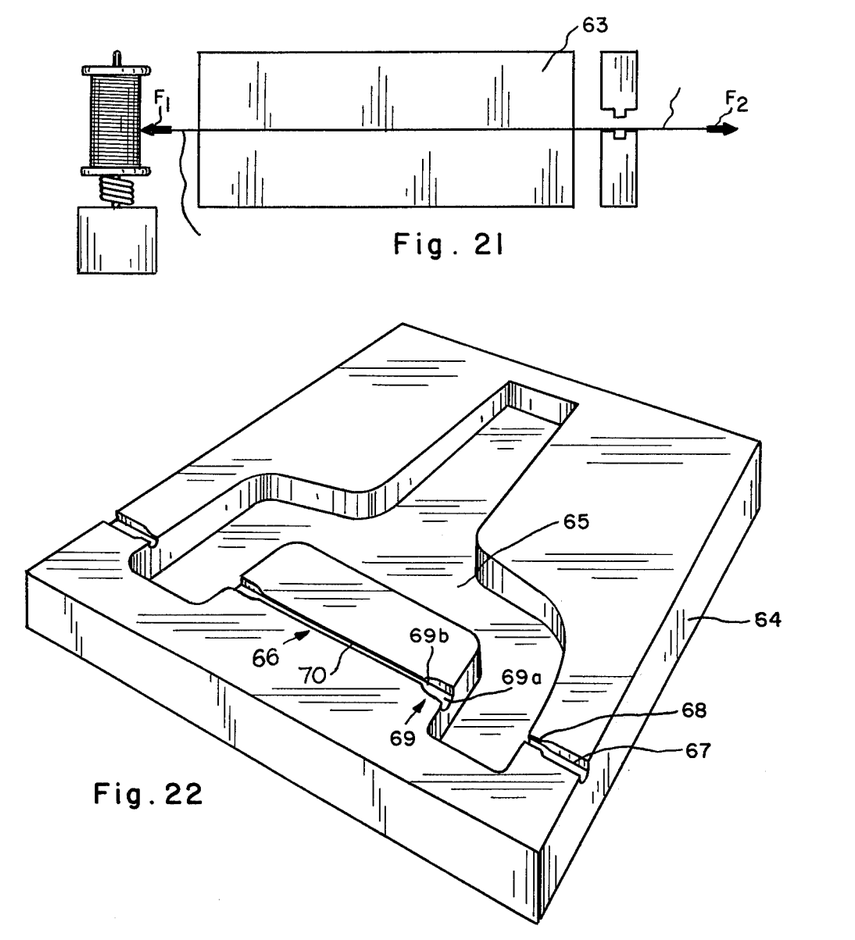
FIG. 21 is a schematic view of a mold with means to tension the floss.
FIG. 22 is a schematic view of a mold where intentional flashing is produced.

In one of the preferred embodiments of the present invention there is the structural feature of intentional flashing; more specifically, the mold cavity is designed to have an incomplete seal at the point where the floss exits the arms, so that during injection a small quantity of fluid plastic will flow or leak out of the cavity and flow along and about the floss for a short distance. This is illustrated in FIG. 22 where mold 64 has basic cavity 65 defining the handle and arms of a flosser with trough 66 in which the floss is placed before the mold is closed. The trough has a first part 67 outward of an arm, a second part 68 immediately adjacent the outer edge of the arm, a third part 69 immediately adjacent the inner edge of the arm, a fourth part 70 intermediate the two arms, and similar parts for the other arm. The first part 67 is substantially wider than the floss to facilitate placement and to help guide the floss into the proper position. The next part 68 is very narrow, having substantially the same diameter as the floss, and thus acts the seal the cavity and prevent or at least greatly inhibit flashing at this point. The third part 69 is a space that is larger than the floss at the exit point 69a immediately adjacent the arm, but tapers to a very small diameter at 69b. In one preferred case part 69 has length not exceeding one third of the length of the central part of the floss spanning the space between the arms of the handle. Plastic flows into this space because part 69a is larger than the floss, and then flows along the length of the floss to part 69b where the flow is essentially stopped. Part 70 is wide like part 67 for ease of positioning the floss.

Figure 23:
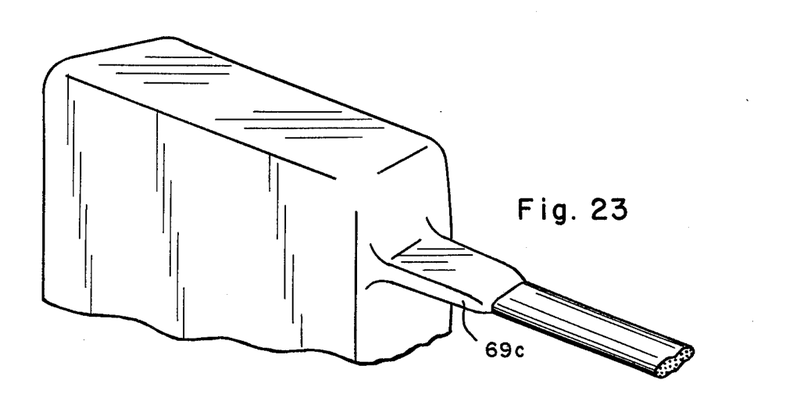
FIG. 23 is a partial front perspective view of a flosser made in a mold shown in FIG. 22.

The plastic in part 69 is "intentional" or "designed" flashing which provides a variety of benefits to the resulting product. The flashing eliminates what could otherwise be a sharp edge of the plastic at the exit point in the arm; it was discovered that this edge often created a stress concentration on the adjacent surface of the floss and ultimate breakage, when the floss was deflected and urged against such edge during use. Secondly, this flashing constitutes support to oppose and reduce deflection, and because of its flexibility, is operative as support even after being deflected. This support is available completely around the floss for 360°, if the flashing flowed in a manner to form a sheath that fully surrounds the floss. Thirdly the flashing extends the plastic of the arm inward, so that a greater length of the floss is embedded; this results in a greater area of the floss being subject to frictional resistance and thus less likelihood of the floss being pulled out of the arms when the high tensile stress developes during use. The end part of the arm of such a flosser with flashing 69c is shown in FIG. 23. As evident from the mold of FIG. 22, the remainder of the flosser would be substantially the same as if made in the mold of FIG. 4.

One preferred flosser developed according to this invention has a circular bow and has dimensions that are considered optimum for the average person's mouth with overall length 3½ inches, bow width — 1¼ inches, floss span between arms of the bow — 15/16 inches, depth of bow from floss to deepest part of bow — 21/32 inches, and thickness of the device 0.080 inches, with all edges and corners rounded. It is optional whether the entire device is disposable, or the bow only, with a re-usable handle.

I claim:

1. A method of making from fluid plastic a solid flosser having a handle part and extending therefrom two arms spaced apart with a strand of floss having a central part spanning the space between said arms and having end-parts embedded within said arms, the method comprising forming a mold and cavity therein defining handle and arm parts corresponding closely to said handle and arm parts of said flosser, positioning the central part of a strand of floss to span the space between said arms of the cavity and said end parts to traverse said arms of the cavity prior to flowing fluid plastic therein, flowing fluid plastic into said cavity by an injection molding process, and thereby embedding with plastic said end parts of the strand in said arm parts of the cavity, and thus coating with said plastic substantially the entire outer peripheral surface of said end-parts, hardening said fluid plastic and thereby in substantially a single step forming said solid flosser and securing said floss end-parts in and integrally with the flosser's arm parts.

2. A method according to claim 1 comprising the further steps of forming an enlargement on at least one of said strand end-parts, and positioning said enlargement along with said end-part in one arm part of the cavity before said fluid plastic is flowed into said cavity.

3. A method according to claim 2 wherein forming said enlargement comprises tying said strand into a knot.

4. A method according to claim 2 wherein forming said enlargement comprises fixedly securing a bead to said strand.

5. A method according to claim 1 comprising the further step of positioning said central part of the strand in a generally straight line configuration between said arms, and positioning at least one end part of the strand in the arm part of the cavity at an angle relative to said central part, whereby this end part has length embedded within the arm part at least 1½ times the length of a line extending through the arm co-axial with said central part.

6. A method of making from fluid plastic a solid flosser having a handle part and at least two spaced-apart floss-engaging portions with a strand of floss having a central part spanning the space between said floss-engaging portions and end-parts of the strand embedded within said floss-engaging portions, comprising forming a mold and cavity therein defining handle and floss-engaging portions corresponding closely to said handle and floss-engaging portions of said flosser, positioning the central part of a strand of floss to span the space between and to traverse said floss-engaging portions of the cavity prior to flowing fluid plastic therein, flowing fluid plastic into said cavity by an injection molding process, and thereby embedding with plastic said end parts of the strand in said floss-engaging portions of the cavity, and thus coating said plastic on substantially the entire outer peripheral surface of said end-parts of the strand of floss, hardening said fluid plastic, and thereby forming said solid flosser and securing said floss end-parts within and integrally with the flosser's floss-engaging portions.

* * * * *